(12) United States Patent
Choi et al.

(10) Patent No.: US 9,616,418 B2
(45) Date of Patent: Apr. 11, 2017

(54) METAL COMPLEX AND SUPPORTED METAL COMPLEX HAVING DISILOXANE AS LIGAND, METHOD FOR PRODUCTION THEREFOR, AND SUPPORTED METAL CATALYST PREPARED BY USING THE SAME

(71) Applicant: NATIONAL INSTITUTE OF ADVANCED INDUSTRIAL SCIENCE AND TECHNOLOGY, Tokyo (JP)

(72) Inventors: Jun-Chul Choi, Tsukuba (JP); Norihisa Fukaya, Tsukuba (JP); Hiroyuki Yasuda, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 14/774,481

(22) PCT Filed: Mar. 13, 2014

(86) PCT No.: PCT/JP2014/056716
§ 371 (c)(1),
(2) Date: Sep. 10, 2015

(87) PCT Pub. No.: WO2014/142252
PCT Pub. Date: Sep. 18, 2014

(65) Prior Publication Data
US 2016/0030932 A1 Feb. 4, 2016

(30) Foreign Application Priority Data
Mar. 14, 2013 (JP) .................. 2013-051526

(51) Int. Cl.
*B01J 29/74* (2006.01)
*C01B 39/46* (2006.01)
(Continued)

(52) U.S. Cl.
CPC .............. *B01J 29/74* (2013.01); *B01J 23/42* (2013.01); *B01J 29/0325* (2013.01); *B01J 31/1633* (2013.01); *B01J 31/1805* (2013.01); *B01J 31/20* (2013.01); *B01J 31/223* (2013.01); *B01J 31/2273* (2013.01); *B01J 31/2295* (2013.01); *B01J 31/24* (2013.01); *B01J 35/002* (2013.01); *B01J 35/006* (2013.01); *B01J 37/08* (2013.01); *B01J 37/086* (2013.01); *C01B 33/20* (2013.01); *C01B 39/46* (2013.01); *C07C 5/03* (2013.01); *C07F 15/006* (2013.01); *C07F 15/0066* (2013.01); *C07F 15/0086* (2013.01); *C07F 15/0093* (2013.01); *B01J 31/1608* (2013.01); *B01J 2231/323* (2013.01); *B01J 2231/645* (2013.01); *B01J 2531/824* (2013.01); *B01J 2531/828* (2013.01); *C07C 2101/18* (2013.01); *C07C 2531/22* (2013.01); *Y02P 20/588* (2015.11)

(58) Field of Classification Search
None
See application file for complete search history.

(56) References Cited

U.S. PATENT DOCUMENTS

| | | |
|---|---|---|
| 3,625,934 A | 12/1971 | Rinse |
| 2003/0083454 A1 | 5/2003 | Marko et al. |
| 2007/0167562 A1 | 7/2007 | Zhou et al. |

FOREIGN PATENT DOCUMENTS

| | | |
|---|---|---|
| EP | 1886726 A1 | 2/2008 |
| EP | 2140940 A2 | 1/2010 |
| EP | 1712277 A1 | 10/2016 |

OTHER PUBLICATIONS

Ruddy et al. Chem. Mater., 2008, 20, 6517-6527.*

(Continued)

*Primary Examiner* — Yun Qian
(74) *Attorney, Agent, or Firm* — Myers Bigel, P.A.

(57) ABSTRACT

A metal complex represented by the following Formula (1):

[CHEM 1]

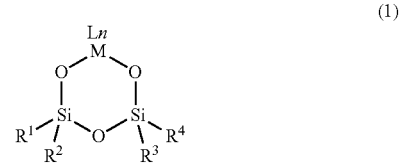

(1)

(wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and each of $R^1$ to $R^4$ represents an organic group. The metal complex described above can be fixed on an inorganic oxide while maintaining a skeletal structure thereof to obtain a supported metal complex, which makes it possible to allow the supported metal complex to maintain the same catalytic activity as that of the original metal complex. Also, calcining the supported metal complex obtained in the manner described above makes it possible to obtain a supported metal catalyst improved in catalytic activity to a greater extent than conventional supported metal catalysts.

5 Claims, 8 Drawing Sheets

(51) Int. Cl.
    *C01B 33/20* (2006.01)
    *B01J 23/42* (2006.01)
    *B01J 37/08* (2006.01)
    *C07F 15/00* (2006.01)
    *B01J 31/16* (2006.01)
    *B01J 35/00* (2006.01)
    *B01J 29/03* (2006.01)
    *B01J 31/18* (2006.01)
    *B01J 31/20* (2006.01)
    *B01J 31/22* (2006.01)
    *B01J 31/24* (2006.01)
    *C07C 5/03* (2006.01)

(56) References Cited

OTHER PUBLICATIONS

Beckmann et al. "Strained Metallastannoxanes—Ring-Opening Polymerization versus Retention of Six-Membered-Ring Structure", *Organometallics* 18(9):1586-1595 (1999).

Hursthouse et al. "Cyclic cobaltadisiloxane compounds. Crystal structures of a pyridinolithium [bis(cyclosiloxy)cobalt] cobalt chloride and a bis(tetramethylethylenediaminolithium)-bis(cyclosiioxy) cobaltate", *J. Organometallic Chem*. 381:C43-C46 (1990).

International Search Report corresponding to International Application No. PCT/JP2014/056716 mailed Jun. 17, 2014.

Choi et al. "Highly Dispersed Pd-SBA15 Materials from Tris(*tert*-butoxy)siloxy Complexes of Pd(II)", *ACS Catalysis* 1(10):1166-1177 (2011).

Judai et al. "Low-Temperature Cluster Catalysis", *J. Am. Chem Soc*. 126(9):2732-2737 (2004).

Lang et al. "Dendrimer-Encapsulated Nanoparticle Precursors to Supported Platinum Catalysts",*J. Am. Chem. Soc*. 125(48):14832-14836 (2003).

Ruddy et al. "Site-Isolated Pt-SBA15 Materials from Tris (*tert*-butoxy)siloxy Complexes of Pt(II0 and Pt(IV)", *Chem. Mater*. 20(20):6517-6527 (2008).

Trong On et al. "Perspectives in catalytic applications of mesostructured materials", *Applied Catalysts A* General 253:545-602 (2003).

Extended European Search Report corresponding to European Application No. 14765042.8 dated Sep. 6, 2016.

Chinese Office Action, Chinese Patent Application No. 201480025536.7, dated Dec. 5, 2016.

\* cited by examiner

20nm

METAL COMPLEX AND SUPPORTED METAL COMPLEX HAVING DISILOXANE AS LIGAND, METHOD FOR PRODUCTION THEREFOR, AND SUPPORTED METAL CATALYST PREPARED BY USING THE SAME

RELATED APPLICATIONS

This application is a 35 U.S.C. §371 national phase application of PCT Application PCT/JP2014/056716 filed Mar. 13, 2014 which claims priority to Japanese Application No. 2013-051526 filed Mar. 14, 2013. The entire contents of each are incorporated herein by reference in its entirety.

BACKGROUND OF THE INVENTION

Technical Field

The present invention relates to a metal complex having a skeletal structure in which a disiloxane group is coordinated as a chelate to a central metal. Further, the present invention relates to a supported metal complex obtained by fixing the metal complex on an inorganic oxide while retaining a skeletal structure thereof, and a method for producing the same.

Also, the present invention relates to a method for producing a supported metal catalyst by calcining the supported metal complex.

Background Art

A reaction system in which a catalyst containing a metal component as a catalytically active component is used can be roughly classified into a homogeneous catalytic system and a heterogeneous catalytic system. In the homogeneous catalytic system, a catalyst such as a metal salt, a metal complex and the like is dissolved or dispersed in a solvent or a reactant and the catalyst is brought into contact with the reactant in a liquid phase to allow a catalytic reaction to proceed. On the other hand, in the heterogeneous catalytic system, a supported metal catalyst prepared by carrying a metal component on a solid carrier is brought into contact with a gas phase or a liquid phase containing a reactant to allow a catalytic reaction to proceed.

In a homogeneous catalytic system, utilization efficiency of the catalyst is usually high, and a catalytic reaction can be allowed to proceed with high activity and high selectivity, but involved therein is the problem that it takes time to separate and recover the catalyst from the reaction product after the reaction.

On the other hand, in a heterogeneous catalytic system, the catalyst is readily separated from the reaction product, and it can be easily applied as well to a flow reaction system in which a catalyst is used in a fixed bed system and in which a reactant is supplied thereto to remove the reaction product in order from the system. Accordingly, heterogeneous catalysts, especially supported metal catalysts, are widely used in the broad fields ranging from petroleum refineries to synthesis of chemicals and environmental cleanup.

In general, a method in which a carrier such as an inorganic oxide is impregnated with a solution containing a metal component such as metal salts and in which the metal is fixed on the carrier after the steps of drying, calcining, reducing and the like has so far been carried out as the production method for a supported metal catalyst as described above. In the foregoing method, however, the metal forms large particles, and therefore it is very difficult to obtain a catalyst in which the metal is evenly dispersed on the carrier at a high dispersion rate.

In order to solve the foregoing problems of the homogeneous catalyst and the supported metal catalyst, it has been considered to fix the metal complex on a solid carrier. If the metal complex having a catalytic activity can be fixed as it is on the carrier, a catalyst having the foregoing advantage involved in the heterogeneous catalyst while maintaining a catalytic activity and a selectivity of the metal complex in a homogeneous system is expected to be obtained. Also, the metal component is expected to be dispersed more evenly on the carrier and fixed thereon by fixing the metal component on the carrier in the form of the metal complex, and calcining the carrier described above allows metal particles having a smaller particle size to be more evenly dispersed and formed on the carrier, whereby a supported catalyst having a higher catalytic activity is expected to be obtained.

In general, a method for fixing a metal complex on an inorganic oxide includes (1) a method in which a metal complex is fixed by making use of a reaction of a hydroxyl group and the like on the surface of an inorganic oxide with a metal and a ligand of a metal complex and (2) a method in which the surface of an inorganic oxide is modified with an organic group such as an amino group, a phosphino group and the like and the like to fix a metal complex using the above organic group as a ligand.

However, in the fixing method of (1), a change (isomerization, clustering, decomposition and the like) in the skeletal structure of the metal complex takes place due to the action of a hydroxyl group and the like on the surface of the inorganic oxide in fixing the metal complex on an inorganic oxide carrier to cause a central metal of the metal complex to be combined directly with the surface of the carrier, and it is difficult to fix the metal complex while maintaining an inherent skeletal structure of the metal complex. Thus, it is difficult to maintain a catalytic activity of the metal complex. Further, it is very difficult to produce a supported metal catalyst in which metal particles having a small particle size are evenly carried on the carrier at a high dispersion rate by calcining the carrier described above.

In connection with the fixing method of (1), Tilley et al. report a method in which in fixing a metal complex on a silica carrier, a metal complex compound having two siloxy groups having three organic leaving groups (R) is utilized in order to fix the metal on the carrier in a mononuclear form (non-patent documents 1 to 2).

However, in the above method, as shown in the following Equation 1, it is reported that the siloxy groups combined with the metal are released instead of the organic leaving groups (R) included in the metal complex and the metal is combined directly with the carrier via an oxygen atom on the surface of the carrier. That is, the skeletal structure of the metal complex is not maintained in the method described above. Further, since the metal is combined with the carrier only by one covalent bond, the bond strength is not sufficiently high, and a metal-metal bond is liable to be formed in a calcining step, so that the metal may be carried on the carrier in the form of metal particles having a large particle size.

[Equation 1]

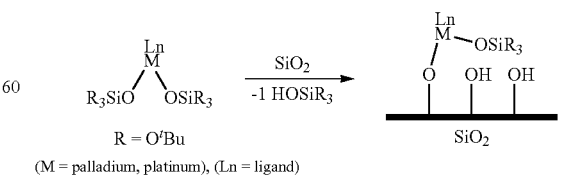

Also, the same change in the skeletal structure can take place as well in the fixing method of (2), and in addition thereto, the carrier itself of the inorganic oxide modified with an organic group such as an amino group, a phosphine group and the like is less resistant to high temperatures, so that it is very difficult to produce a metal catalyst in which metal particles are evenly carried on the carrier by calcining the carrier described above.

As described above, the inherent skeletal structure of the metal complex cannot be maintained in the conventional methods for fixing a metal complex on an inorganic oxide carrier, and a change (isomerization, clustering, decomposition and the like) in the skeletal structure takes place, so that it is difficult to maintain a catalytic activity of the metal complex. Further, involved therein is the problem that a metal-metal bond is readily formed by calcining the carrier described above and that it is very difficult to obtain a supported metal catalyst in which fine particles of the catalyst metal are evenly carried on the carrier at a high dispersion rate.

CITATION LIST

Non-patent document 1: Chem. Mater., vol. 20, p. 6517 (2008)
Non-patent document 2: ACS Catal., vol. 1, p. 1166 (2011)

SUMMARY OF INVENTION

A first object of the present invention is to provide a metal complex which can be fixed on an inorganic oxide carrier while retaining a skeletal structure of the original metal complex, and to provide a supported metal complex in which the metal complex is fixed on a carrier to maintain the same catalytic activity as that of the original metal complex.

Also, a second object of the present invention is to provide a supported metal catalyst in which metal is dispersed and carried more evenly on a carrier in smaller sizes than conventional supported metal catalysts by calcining the supported metal complex obtained in the manner described above and in which a catalytic activity is enhanced by the processing described above.

Intense research by the present inventors in order to solve the problems described above have resulted in finding that a metal complex newly prepared by the present inventors and having a skeletal structure in which a disiloxane group is coordinated as a chelate to a central metal is surprisingly fixed on an inorganic oxide while retaining the skeletal structure thereof and that this makes it possible to maintain the same catalytic activity as that of the original metal complex.

Further, the present inventors have found that calcining the supported metal complex obtained in the manner described above makes it possible to obtain a supported metal catalyst which is improved in a catalytic activity to a larger extent than conventional supported metal catalysts.

The present invention has been completed based on such new findings as described above.

That is, the present application provides the following inventions.

(1) A metal complex represented by the following Formula (1):

[CHEM 1]

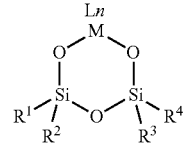

(1)

(wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and each of $R^1$ to $R^4$ represents an organic group).

(2) A supported metal complex having a structure represented by the following Formula (2), in which the metal complex is fixed on an inorganic oxide:

[CHEM 2]

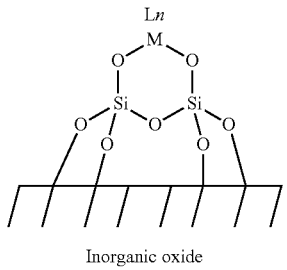

(2)

(wherein M represents palladium or platinum; L represents a ligand selected from carbon monoxide, an olefin compound, an amine compound, a phosphine compound, an N-heterocyclic carbene compound, a nitrile compound and an isocyanide compound; and n represents an integer of 0 to 2 showing the number of the ligand).

(3) The supported metal complex according to the above item (2), wherein the inorganic oxide may be silica or a composite oxide containing silicon.

(4) A method for producing the metal complex as defined in the above item (1), comprising reacting a metal complex $L_nMX_2$ (wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and X represents halogen or a hydroxyl group) with a disiloxane compound HO—($R^1$)($R^2$)Si—O—($R^3$)($R^4$)Si—OH (each of $R^1$ to $R^4$ represents an organic group) in the presence of an alkaline metal hydride.

(5) A method for producing the supported metal complex as defined in the above item (2) or (3), comprising contacting an organic solvent solution of a metal complex represented by the following Formula (3) with an inorganic oxide, to support the metal complex on the inorganic oxide:

[CHEM 3]

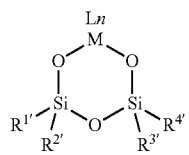

(3)

(wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and each of $R^{1'}$ to $R^{4'}$ represents an alkoxy group having 1 to 4 carbon atoms).

(6) A supported metal catalyst obtained by applying a heat treatment to the supported metal complex as defined in the above item (2) or (3) at a temperature of the range from 80 to 600° C. under an oxygen atmosphere.

(7) A catalyst for hydrogenation reaction of olefins, comprising the supported metal catalyst as defined in the above item (6).

(8) The catalyst for hydrogenation reaction according to the above item (7), wherein a central metal of the catalyst may be platinum.

(9) A catalyst for hydrosilylation reaction of olefins, comprising the metal complex compound as defined in the above item (1).

(10) A catalyst for hydrosilylation reaction of olefins, comprising the supported metal complex as defined in the above item (2) or (3).

(11) The catalyst for hydrosilylation reaction according to the above item (9) or (10), wherein a central metal of the catalyst may be platinum.

Using the metal complex represented by Formula (1) having a skeletal structure in which a disiloxane group is coordinated as a chelate to a central metal, which is provided by the present invention, makes it possible to fix the metal complex on an inorganic oxide while maintaining the skeletal structure thereof, and the obtained supported metal complex can maintain the same catalytic activity as that of the original metal complex. Further, a supported metal catalyst which is improved in a catalytic activity to a large extent as compared with supported metal catalysts prepared by conventional methods can be obtained by calcining the obtained supported metal complex.

DESCRIPTION OF THE PREFERRED EMBODIMENTS

Figure 1:
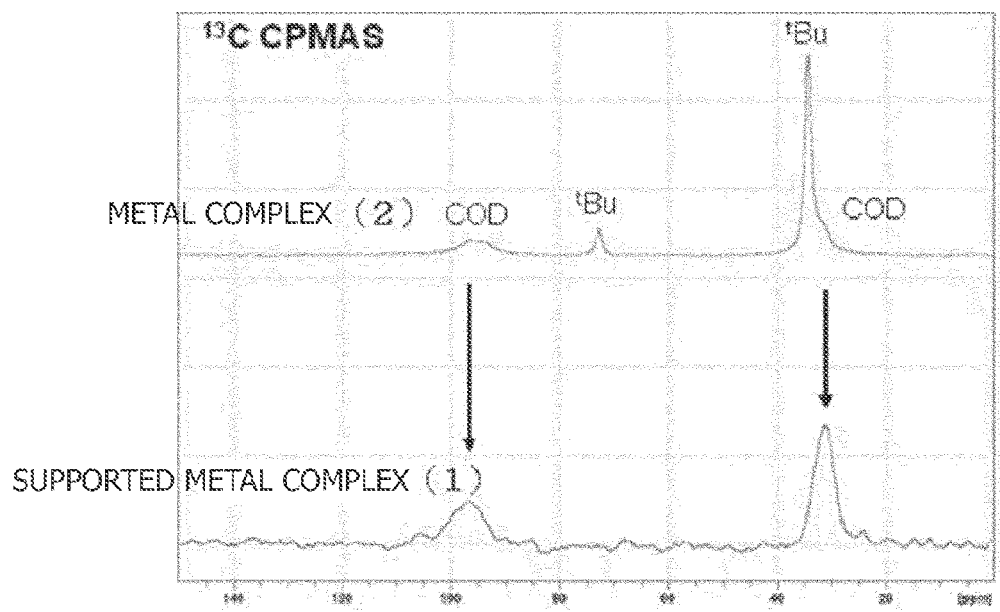
FIG. 1 is a drawing for comparing the $C^{13}$ CPMAS NMR spectra of the metal complex (2) (Example 2) and the supported metal complex (1) (Example 4) of the present invention.

The metal complex of the present invention is represented by the following Formula (1):

[CHEM 1]

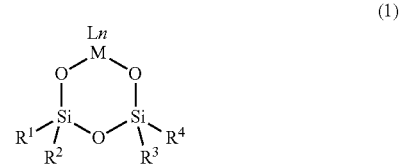

(1)

(wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and each of $R^1$ to $R^4$ represents an organic group).

The ligand L is not particularly limited as long as it can substantially form a coordinate bond with a central metal, and the ligand includes carbon monoxide; an olefin compound such as 1,5-cyclooctadiene (COD), 1,3-cyclopentadiene, 1,2,3,4,5-pentamethylcyclopentadiene, 2,5-norbornadiene, ethylene, dibenzylideneacetone, and the like; an amine compound such as, 2,2'-bipyridyl, 1,10-phenanthroline, ethylenediamine, 1,2-bis(dimethylamino)ethane, 1,2-diphenylethylenediamine, 1,2-cyclohexanediamine, and the like; a phosphine compound such as trimethylphosphine, triethylphosphine, triisopropylphosphine, tri-tert-butylphosphine, tricyclohexylphosphine, triphenylphosphine, dimethylphenylphosphine, trimethylphosphite, triethylphosphite, triisopropylphosphite, tri-tert-butylphosphite, triphenylphosphite, methyldiphenylphosphite, 1,2-bis(dimethylphosphino)ethane, 1,2-bis(diphenylphosphino)ethane, 1,3-bis(dimethylphosphino)propane, diphenylphosphinoferrocene, and the like; an N-heterocyclic carbene compound such as 1,3-bis(2,6-diisopropylphenyl)imidazolidine-2-ylidene, 1,3-bis(2,6-diisopropylphenyl)imidazole-2-ylidene, 1,3-di-tert-butylimidazole-2-ylidene, 1,3-bis(2,4,6-trimethylphenyl)imidazolidine-2-ylidene, 1,3-bis(2,4,6-trimethylphenyl)imidazole-2-ylidene, 1,3-di(1-adamantyl)imidazolidine-2-ylidene, 1,3-di(1-adamantyl)imidazole-2-ylidene, 1,3-dicyclohexylimidazole-2-ylidene, and the like; a nitrile compound such as benzonitrile, acetonitrile and the like; and an isocyanide compound such as tert-butyl isocyanide, 1,1,3,3-tetramethylbutyl isocyanide and the like. Among them, 1,5-cyclooctadiene, dibenzylideneacetone, trimethylphosphine, triethylphosphine, tri-tert-butylphosphine, triphenylphosphine and the like are preferred, and 1,5-cyclooctadiene and trimethylphosphine are further preferred.

Also, n represents an integer of 0 to 2 showing the number of the ligand. When the ligand is a bidentate ligand such as 1,5-cyclooctadiene, n is usually 1, and when the ligand is a monodentate ligand such as trimethylphosphine, n is usually 2.

Substantially, any of the organic groups can be used independently as the organic groups $R^1$ to $R^4$, and from the viewpoint of making it possible to fix the metal complex on the inorganic oxide, they are preferably an alkoxy group and an amino group each having a hydrolyzability, particularly preferably an alkoxy group.

The metal complex of the present invention can be synthesized, for example, by reacting a metal complex $L_nMX_2$ (wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and X represents halogen or a hydroxyl group) with a disiloxane compound HO—$(R^1)(R^2)$Si—O—$(R^3)(R^4)$Si—OH (each of $R^1$ to $R^4$ represents an organic group) under the presence of an alkaline metal hydride.

The supported metal complex of the present invention has a structure represented by the following Formula (2):

[CHEM 2]

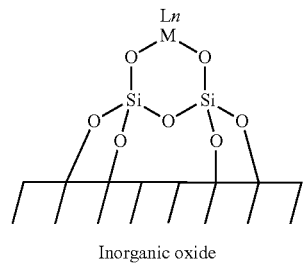

(2)

(wherein M represents palladium or platinum; L represents a ligand selected from carbon monoxide, an olefin compound, an amine compound, a phosphine compound, an N-heterocyclic carbene compound, a nitrile compound and an isocyanide compound; and n represents an integer of 0 to 2 showing the number of the ligand).

The inorganic oxide used in the present invention is not particularly limited, and single oxides of silicon, titanium, aluminum, zirconium, magnesium and the like, and composite oxides containing them can be used. Among them, silica as a silicon oxide, for example, amorphous silica, or composite oxides containing silica, for example, aluminosilicate, are preferably used from the viewpoints of containing numerous silanol groups as a hydroxyl group on the surface and enabling to form a strong covalent bond between the organic leaving group and the inorganic oxide. Furthermore, regular mesoporous silica or regular mesoporous metallosilicate such as MCM-41, SBA-15 and the like, zeolite such as crystalline aluminosilicate, metallosilicate, aluminophosphate, silica-aluminophosphate, and the like, porous glass, clay minerals, and the like are also preferably used from the viewpoint of enabling increase in introduced amount of the metal complex per unit weight by making use of a large surface area thereof. The inorganic oxide used in the present invention may be either compounds synthesized by known methods or commercially available products.

The inorganic oxides have preferably an average pore diameter of 0.5 to 500 nm, more preferably an average pore diameter of 1 to 100 nm. Also, the inorganic oxides having a large surface area are preferred in order to combine the metal complex with the inorganic oxide at a high density, and the inorganic oxides having a specific surface area of, for example, 100 to 1500 $m^2/g$ are preferred.

The supported metal complex of the present invention can be obtained, for example, by contacting an organic solvent solution of a metal complex represented by the following Formula (3) with an inorganic oxide:

[CHEM 3]

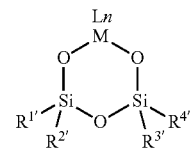

(3)

(wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 0 to 2 showing the number of the ligand; and each of $R^{1'}$ to $R^{4'}$ represents an alkoxy group having 1 to 4 carbon atoms).

An inorganic oxide may be suspended in a solution prepared by dissolving the metal complex represented by Formula (3) in an organic solvent, and the suspension may be stirred at room temperature or while heating. Then, solids may be combined by filtering and this is washed and dried to thereby obtain a supported metal complex. The organic solvent includes, for example, aliphatic hydrocarbons such as pentane, hexane and the like, aromatic hydrocarbons such as toluene, xylene and the like, and ethers such as diethyl ether, dibutyl ether and the like, and they may be used alone or in a mixture.

The metal complex represented by Formula (3) can be reacted with the inorganic oxide, whereby a part or all of the organic groups $R^{1'}$ to $R^{4'}$ may be eliminated, and a supported metal complex retaining an inherent skeletal structure of the metal complex can be obtained.

A supported metal amount of the supported metal complex thus obtained can be determined by analysis such as ICP-OES and the like.

In the supported metal complex of the present invention, the metal complex carried on the carrier may retain the skeletal structure of the metal complex before carried, and therefore the supported metal complex can maintain a catalytic action of the metal complex before being carried.

As confirmed in, for example, Examples 14 and 15, described later, the supported metal complex (1) of the present invention may have a catalyst activity, as is the case with the corresponding metal complex (2) before being carried, in a hydrosilylation reaction of olefins, for example, a hydrosilylation reaction of norbornene.

The supported metal catalyst of the present invention can be obtained by calcining the supported metal complex of the present invention at a temperature of 80 to 600° C. under an oxygen atmosphere. Either oxygen or air may be used for the oxygen atmosphere. A carried metal amount of the supported metal catalyst thus obtained can be determined by analysis such as ICP-OES and the like.

The supported metal catalyst of the present invention can be used for various catalytic reactions in which conventional supported platinum catalysts and supported palladium catalysts are used.

A method for evaluating an activity of the supported metal catalyst of the present invention is not particularly limited, and the activity thereof can be evaluated by investigating, for example, a hydrogenation reaction of olefins, which is a representative catalytic reaction with platinum metal species, for example, a hydrogenation reaction of cyclooctene.

As confirmed in Examples 11 to 13 described later, the supported metal catalyst of the present invention may be improved in a catalytic activity to a large extent in a hydrogenation reaction of olefins as compared with conventional supported metal catalysts. This may be attributable to the fact that the supported metal catalyst of the present invention is formed by evenly dispersing the fine particles of the catalyst metal on a carrier, and it is apparent that a similar improvement in the catalyst activity is obtained in other catalytic reactions.

The present invention shall be explained in further detail with reference to Examples and Reference Examples shown below.

EXAMPLES

Example 1

Synthesis of Metal Complex (1)

45 ml of THF solution containing HO[(tert-BuO)$_2$SiO]$_2$H (able to be synthesized by a method described in, for example, J. Beckmann, et. al., Appl. Organometal. Chem., vol. 17, p. 52 (2003), and the like) (1.02 g, 2.6 mmol) and KH (0.24 g, 6 mmol) was dropwise added to a 200 ml volume Schlenk tube containing (COD) PdBr$_2$ (0.9 g, 2.4 mmol) and 20 ml of THF solvent, and they were reacted for 2 hours. The reaction liquid was filtered, and a matter obtained was dried under vacuum to thereby obtain the following metal complex (1) 1.1 g. The metal complex (1) was subjected to structure identification by a solution NMR spectrum.

[CHEM 4]

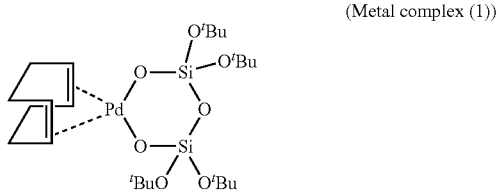

(Metal complex (1))

Solution NMR (room temperature, solvent (C$_6$D$_6$))
$^1$H NMR (400 MHz); δ 1.26, 1.33, 2.71

Example 2

Synthesis of Metal Complex (2)

A metal complex (2) 1.51 g was obtained by carrying out the same procedure as in Example 1, except that (COD) PtI$_2$ (1.34 g, 2.4 mmol) was used. The metal complex (2) was subjected to structure identification by a solution NMR spectrum and elemental analysis (C, H analysis). Further, the NMR spectrum of the solid matter was measured for structure identification in a solid state (refer to FIGS. 1 and 2).

[CHEM 5]

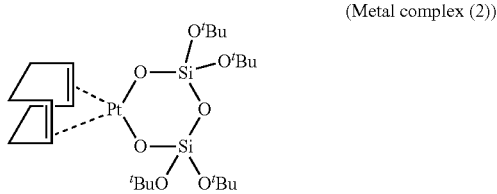

(Metal complex (2))

Solution NMR (room temperature, solvent (C$_6$D$_6$))
(1) $^1$H NMR (400 MHz); δ 1.09, 1.63, 1.70, 4.66
(2) $^{13}$C {$^1$H} NMR; δ 29.7, 31.1, 71.7, 91.3
(3) $^{29}$Si {$^1$H} NMR; δ −84.9
Elemental analysis (C$_{24}$H$_{48}$O$_7$Si$_2$Pt$_1$)
(1) theoretical value: C, 41.19; H, 6.91%
(2) measured value: C, 41.67; H, 6.92%

Example 3

Synthesis of Metal Complex (3)

A metal complex (3) 1.61 g was obtained by carrying out the same procedure as in Example 1, except that $(Me_3P)_2PtI_2$ (1.44 g, 2.4 mmol) was used. The metal complex (3) was subjected to structure identification by a solution NMR spectrum and elemental analysis (C, H analysis).

[CHEM 6]

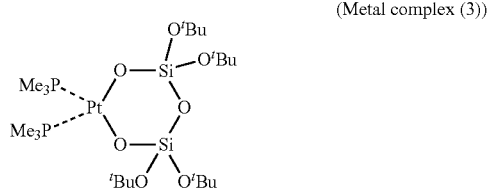

(Metal complex (3))

Solution NMR (room temperature, solvent ($CD_2Cl_2$))
(1) $^1H$ NMR (400 MHz); δ 1.31, 1.54-1.58
(2) $^{13}C$ {$^1H$} NMR; δ 14.2-14.8, 31.2, 40.4
(3) $^{31}P$ {$^1H$} NMR; δ −26.95
Elemental analysis ($C_{22}H_{54}P_2Si_2Pt_1$)
(1) theoretical value: C, 35.52; H, 7.32%
(2) measured value: C, 35.59; H, 7.15%

Example 4

Synthesis of Supported Metal Complex (1)

Mesoporous silica MCM-41 (able to be synthesized by a method described in, for example, C. T. Kresge, et. al., Nature, vol. 359, p. 710 (1992) and the like) (5 g) was dried at 120° C. for 1 hour under reduced pressure. The reaction system was cooled to room temperature, and then an inside thereof was replaced with a dry nitrogen gas. The metal complex (2) (0.18 g, 0.26 mmol) and toluene (100 ml) were added thereto, and the mixture was stirred at room temperature for 24 hours. The resulting solid matter was filtered and washed three times with toluene (100 ml). Then, the solid matter was dried at room temperature for 24 hours under reduced pressure to obtain a supported metal complex (1).

Figure 3:
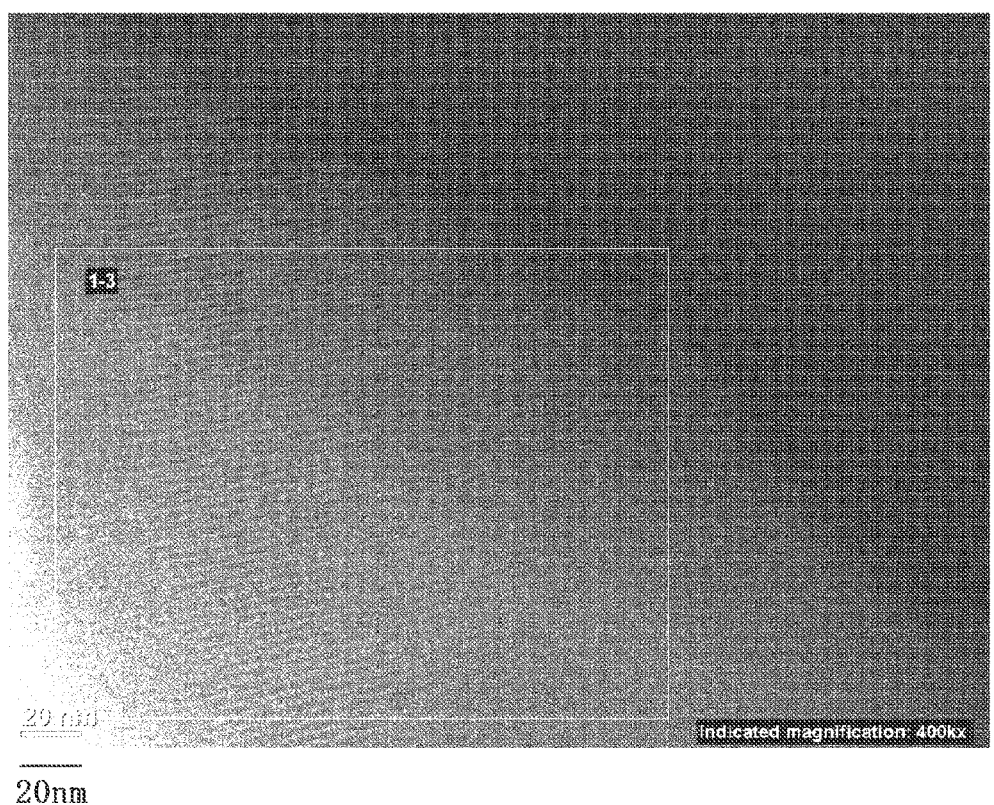
FIG. 3 is a scanning transmission electron microscope (STEM) observation drawing of the supported metal complex (1) (Example 4) of the present invention.
Figure 4:
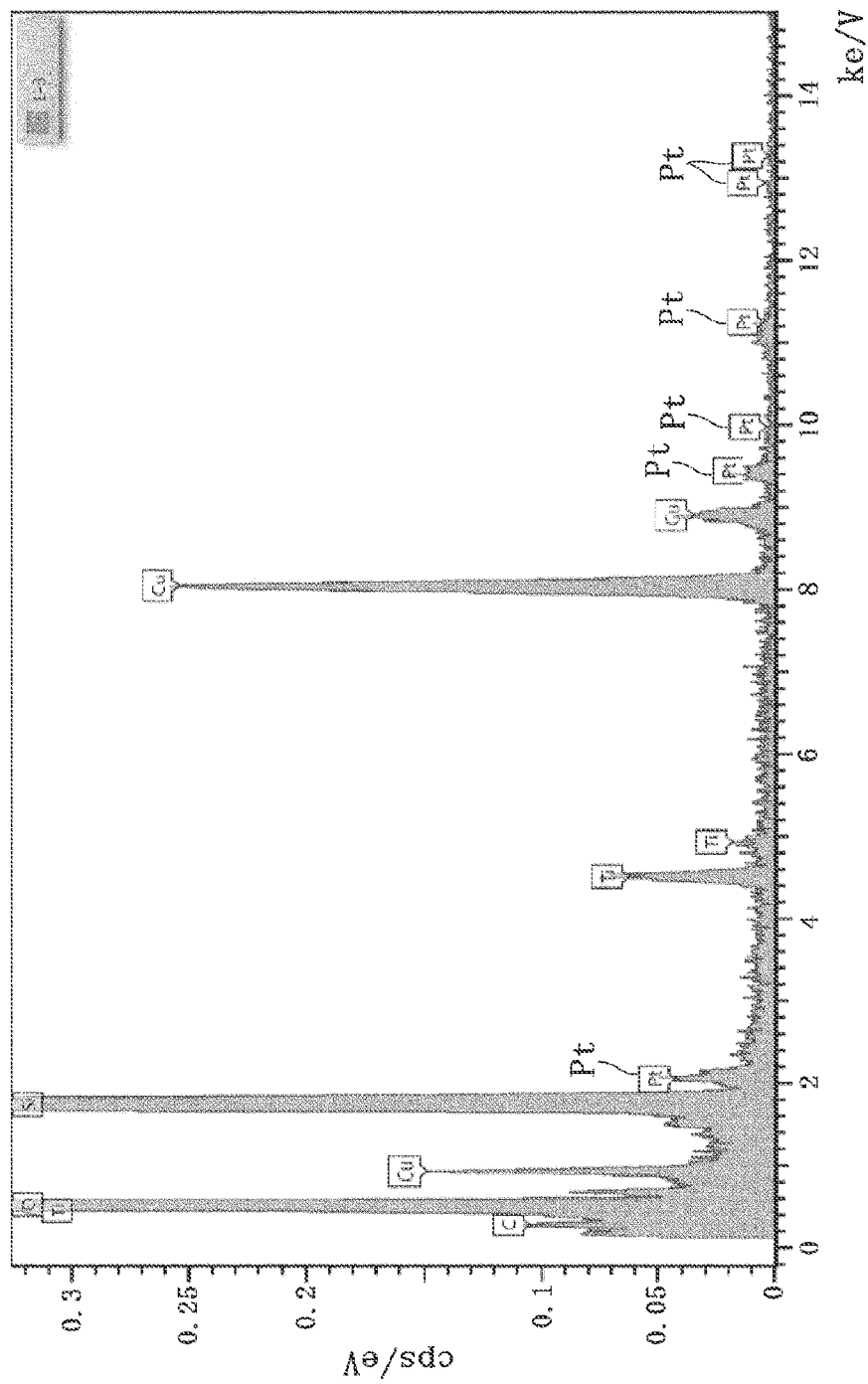
FIG. 4 is an energy dispersive X-ray (EDX) analytical drawing of the supported metal complex (1) (Example 4) of the present invention.

The solid NMR spectrum of the supported metal complex (1) was compared with that of the metal complex (2) to thereby analyze a connecting state of the metal complex (2) to the mesoporous silica carrier. The results obtained by measuring the metal complex (2) and the supported metal complex (1) by $^{13}C$ CPMAS NMR and $^{29}Si$ CPMAS NMR were shown in FIGS. 1 and 2. The peaks observed can be assigned to COD, a t-Bu group and Si as shown respectively in the drawings, and the above assignment resulted in confirming that the metal complex (2) was connected, as shown in [Chem 7], to the mesoporous silica while eliminating four t-Bu groups and that the supported metal complex (1) was obtained. Further, the supported metal complex (1) was subjected to scanning transmission electron microscope (STEM) observation and energy dispersive X-ray (EDX) analysis. The results of the STEM observation and the EDX analysis are shown in FIGS. 3 and 4. Platinum was apparently present according to the EDX analysis, but platinum particles could not be confirmed to be present by the STEM observation. The above finding resulted in confirming that platinum was carried on the mesoporous silica carrier in a state of a monoatom while retaining the original complex structure. An amount of platinum carried on the supported metal complex (1) thus obtained was determined by an ICP-OES method to result in finding that it was 1.06% by weight.

[Chem 7]

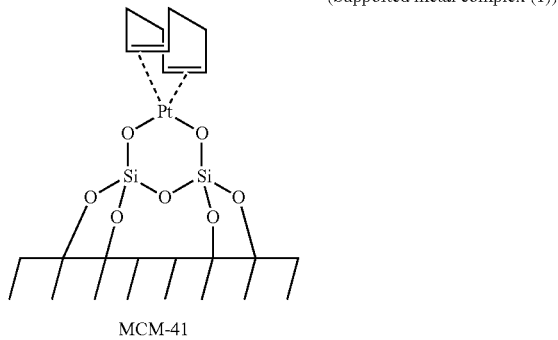

(Supported metal complex (1))

Example 5

Synthesis of Supported Metal Complex (2)

A supported metal complex (2) was obtained by carrying out the same procedure as in Example 4, except that the metal complex (3) (0.39 g, 0.52 mmol) was used.

[CHEM 8]

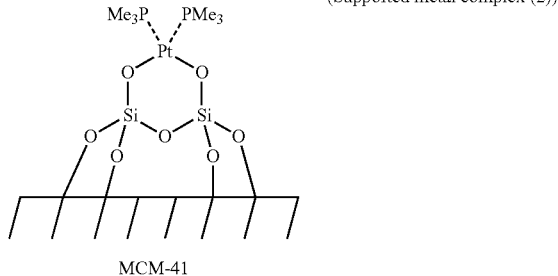

(Supported metal complex (2))

Example 6

Synthesis of Supported Metal Complex (3)

A supported metal complex (3) was obtained by carrying out the same procedure as in Example 4, except that amorphous silica (CARiACT Q-10, manufactured by Fuji Silysia Chemical Ltd., surface area: 250 m²/g) was used as the carrier.

Figure 2:
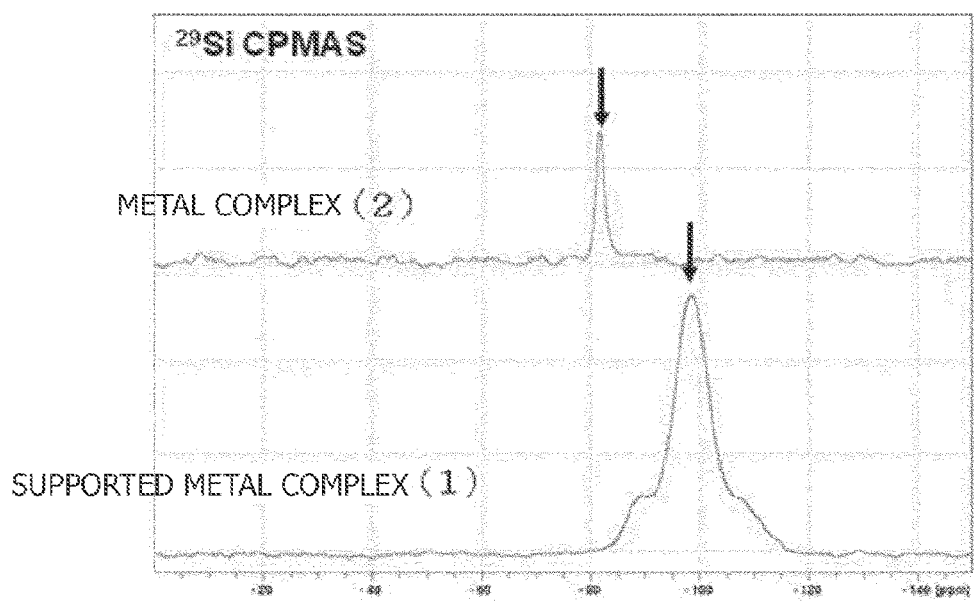
FIG. 2 is a drawing for comparing the $^{29}Si$ CPMAS NMR spectra of the metal complex (2) (Example 2) and the supported metal complex (1) (Example 4) of the present invention.

The results obtained by measuring the supported metal complex (3) by $^{13}C$ CPMAS NMR and $^{29}Si$ CPMAS NMR were the same as in FIGS. 1 and 2, and the above matter resulted in confirming that the metal complex (2) was connected, as shown in [CHEM 9], to the amorphous silica while eliminating four t-Bu groups and that the supported metal complex (3) was obtained.

[CHEM 9]

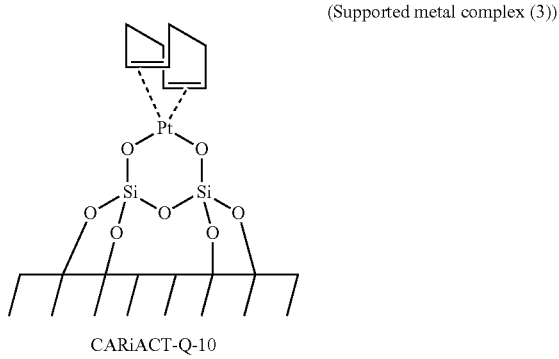

(Supported metal complex (3))

CARiACT-Q-10

Example 7

Synthesis of Supported Metal Complex (4)

A supported metal complex (4) was obtained by carrying out the same procedure as in Example 4, except that the metal complex (2) (0.36 g, 0.52 mmol) was used.

Example 8

Synthesis of Supported Metal Catalyst (1)

2 g of the supported metal complex (1) was calcined at 300° C. for 3 hours in an oxygen flow to thereby obtain 1.9 g of a supported metal catalyst (1). An amount of platinum carried on the supported metal catalyst (1) thus obtained was determined by the ICP-OES method to result in finding that it was 1.04% by weight.

Example 9

Synthesis of Supported Metal Catalyst (2)

1.8 g of a supported metal catalyst (2) was obtained by carrying out the same procedure as in Example 8, except that 2 g of the supported metal complex (3) was used. An amount of platinum carried on the supported metal catalyst (2) thus obtained was determined by the ICP-OES method to be 1.03% by weight.

Example 10

Synthesis of Supported Metal Catalyst (3)

Figure 5:
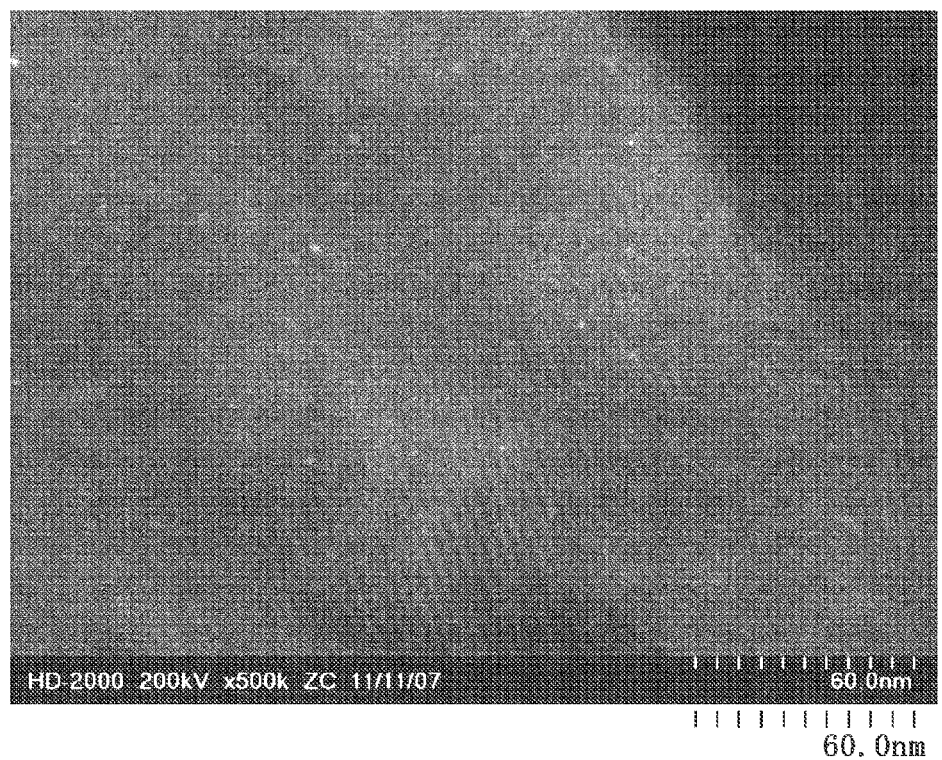
FIG. 5 is a scanning transmission electron microscope (STEM) observation drawing of the supported metal catalyst (3) (Example 10) of the present invention.

1.9 g of a supported metal catalyst (3) was obtained by carrying out the same procedure as in Example 8, except that 2 g of the supported metal complex (4) was used. The supported metal catalyst (3) was observed under STEM. The result thereof was shown in FIG. 5. Platinum was observed to be dispersed and carried relatively evenly on the mesoporous silica carrier in the form of small particles having a size of 2 to 3 nm or less. An amount of platinum carried on the supported metal catalyst (3) thus obtained was determined by the ICP-OES method to result in finding that it was 2.04% by weight.

REFERENCE EXAMPLES

Synthesis of Supported Metal Catalysts by Conventional Technologies

Reference Example 1

Synthesis of Supported Metal Catalyst (4)

50 mL of an aqueous solution containing 0.1 g of $(NH_3)_4Pt(NO_3)_2$ was added dropwise to 5 g of mesoporous silica MCM-41 to thereby impregnate the silica with the solution, and then the mixture was dried at 60° C. for 3 hours under vacuum. The resulting powder was calcined at 300° C. for 3 hours in an oxygen flow to thereby obtain 5.1 g of a supported metal catalyst (4) containing platinum carried on the mesoporous silica. An amount of platinum carried on the supported metal catalyst (4) thus obtained was determined by the ICP-OES method to result in finding that it was 0.92% by weight.

Reference Example 2

Synthesis of Supported Metal Catalyst (5)

A supported metal catalyst (5) was obtained by carrying out the same procedure as in Reference Example 1, except that the amorphous silica CARiACT Q-10 was used as the carrier. An amount of platinum carried on the supported metal catalyst (5) thus obtained was determined by the ICP-OES method to result in finding that it was about 0.91% by weight.

Reference Example 3

Synthesis of Supported Metal Catalyst (6)

Figure 6:
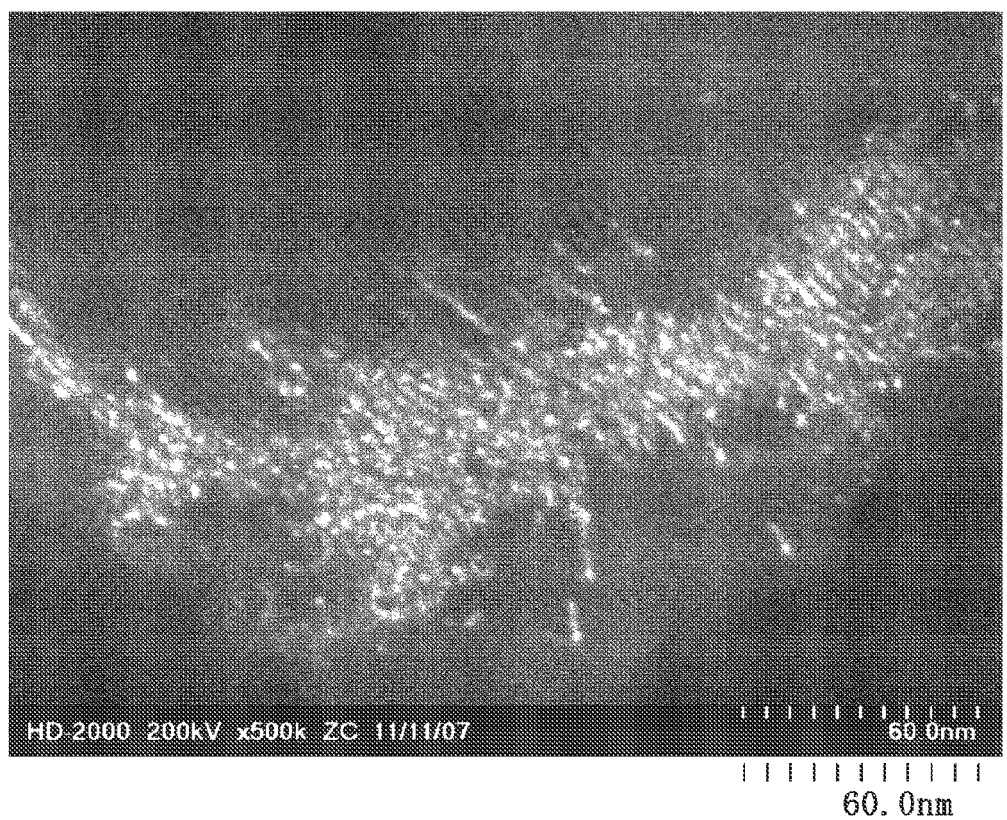
FIG. 6 is a scanning transmission electron microscope (STEM) observation drawing of the supported metal catalyst (6) (Reference Example 3) of the conventional technology.

A supported metal catalyst (6) was obtained by carrying out the same procedure as in Reference Example 1, except that 50 mL of an aqueous solution containing 0.2 g of $(NH_3)_4Pt(NO_3)_2$ was used. An amount of platinum carried on the supported metal catalyst thus obtained was determined by the ICP-OES method to result in finding that it was about 1.68% by weight. The supported metal catalyst (6) was observed under STEM. The result thereof is shown in FIG. 6. It was confirmed that while a carried amount of platinum was small as compared with the supported metal catalyst (3), platinum was aggregated and present unevenly on the mesoporous silica carrier.

[Evaluation of Catalytic Activity of Supported Metal Catalysts in Hydrogenation Reaction]

The catalytic activities of the supported metal catalysts in hydrogenation reaction were evaluated using cyclooctene as olefin and hydrogen as a hydrogen source.

Example 11

Figure 7:
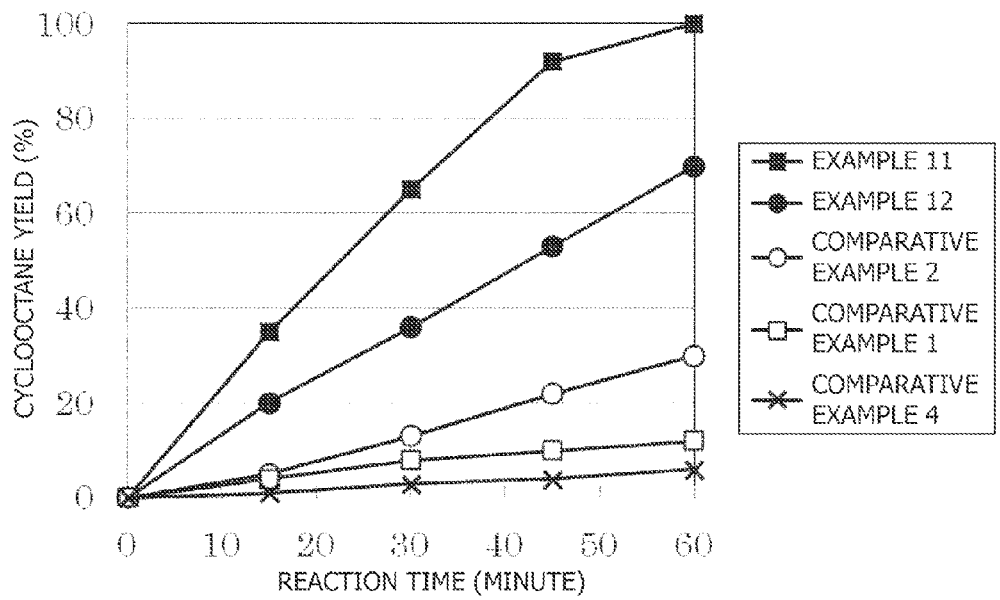
FIG. 7 is a drawing for comparing the catalytic activities in a hydrogenation reaction of cyclooctene carried out by using the supported metal catalysts (1) and (2) (Examples 11 and 12) of the present invention, and the supported metal catalysts (4) and (5) and commercially available platinum silica catalysts (Comparative Examples 1, 2 and 4) according to the conventional technologies.

20 mg of the supported metal catalyst (1) obtained in Example 8 was weighed into a Schlenk tube having a volume of 25 ml and subjected to reduction treatment at 300° C. for 1 hour in a hydrogen flow. After the Schlenk tube was cooled down to room temperature, the Schlenk tube was replaced in an inside with an argon gas and charged with 5 mL of isopropanol containing 120 μL of mesitylene as a standard substance, and 2.5 mmol of cyclooctene. Then, the Schlenk tube was replaced in an inside again with a hydrogen gas, and they were reacted at room temperature under hydrogen at a pressure of 1 atmosphere while stirring. The catalytic activity was evaluated by a change with the passage of time in a yield of cyclooctane which was the product. The result thereof is shown in FIG. 7.

Example 12

The catalytic activity was evaluated by carrying out the same procedure as in Example 11, except that the supported metal catalyst (2) obtained in Example 9 was used. The result thereof is shown together in FIG. 7.

Example 13

Figure 8:
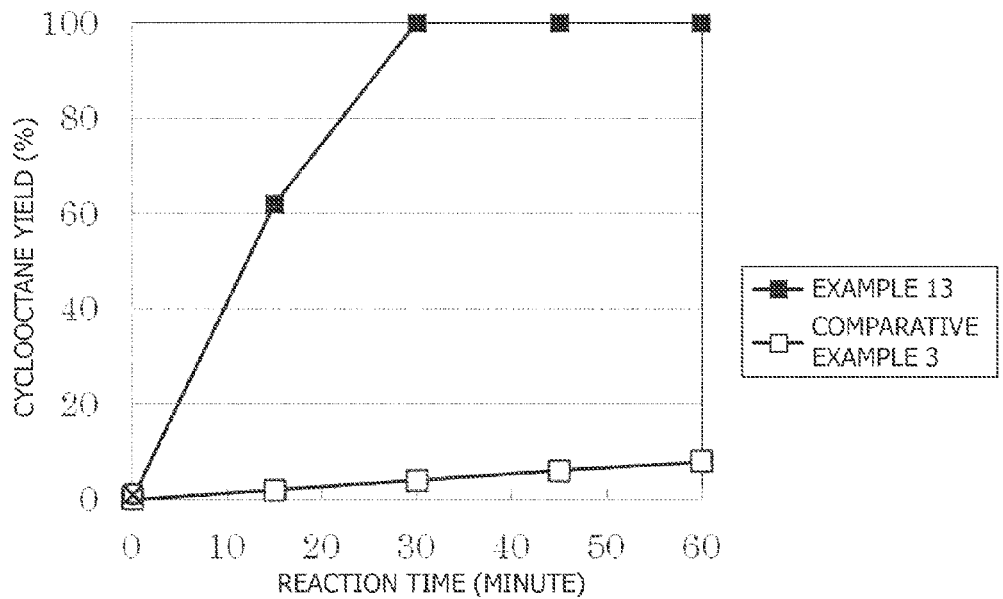
FIG. 8 is a drawing for comparing the catalytic activities in a hydrogenation reaction of cyclooctene carried out by using the supported metal catalyst (3) (Example 13) of the present invention and the supported metal catalyst (6) (Comparative Example 3) according to the conventional technology.

The catalytic activity was evaluated by carrying out the same procedure as in Example 11, except that the supported metal catalyst (3) obtained in Example 10 was used. The result thereof is shown in FIG. 8.

Comparative Example 1

The catalytic activity was evaluated by carrying out the same procedure as in Example 11, except that the supported metal catalyst (4) obtained in Reference Example 1 was used. The result thereof is shown together in FIG. 7.

Comparative Example 2

The catalytic activity was evaluated by carrying out the same procedure as in Example 11, except that the supported metal catalyst (5) obtained in Reference Example 2 was used. The result thereof is shown together in FIG. 7.

Comparative Example 3

The catalytic activity was evaluated by carrying out the same procedure as in Example 11, except that the supported metal catalyst (6) obtained in Reference Example 3 was used. The result thereof is shown together in FIG. 8.

Comparative Example 4

The catalytic activity was evaluated by carrying out the same procedure as in Example 11, except that a commercially available 1 weight % platinum silica catalyst (manufactured by Sigma-Aldrich Corporation) was used. The result thereof is shown together in FIG. 7.

[Evaluation of Catalytic Activity of Metal Complex and Supported Metal Complex in Hydrosilylation Reaction]

The catalytic activities of the metal complexes and the supported metal complexes of the present invention in hydrosilylation reaction by dimethylchlorosilane using norbornene as olefin were evaluated.

[Equation 2]

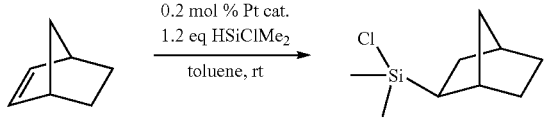

Example 14

Figure 9:
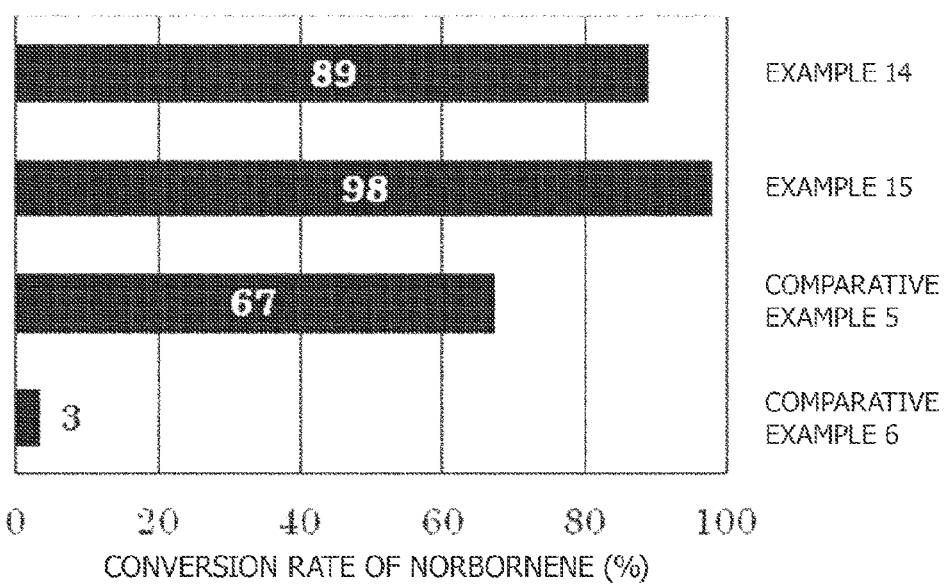
FIG. 9 is a drawing for comparing the catalytic activities (conversion rates of norbornene) in a hydrosilylation reaction of norbornene carried out by using the supported metal complex (1) and the metal complex (2) (Examples 14 and 15) according to the present invention, and platinum catalysts (chloroplatinic acid and the commercially available platinum silica catalyst) (Comparative Examples 5 and 6) according to the conventional technologies.
Figure 10:
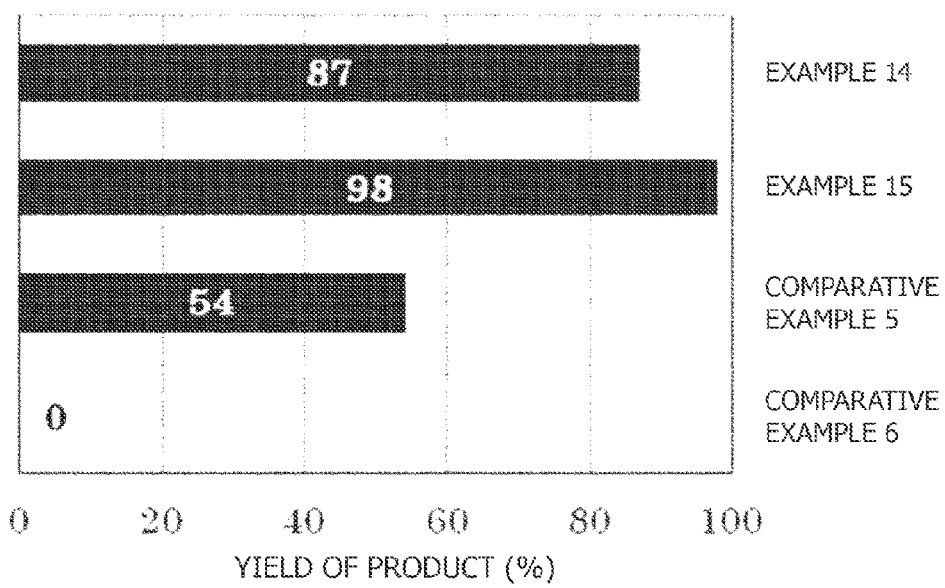
FIG. 10 is a drawing for comparing the catalytic activities (yields of the hydrosilylation product) in a hydrosilylation reaction of norbornene carried out by using the supported metal complex (1) and the metal complex (2) (Examples 14 and 15) according to the present invention, and platinum catalysts (chloroplatinic acid and the commercially available platinum silica catalyst) (Comparative Examples 5 and 6) according to the conventional technologies.

The supported metal complex (1) obtained in Example 5 was weighed into a Schlenk tube having a volume of 25 ml in a proportion of 0.2 mol % based on 1.2 mmol of norbornene as shown in Equation 2 and subjected to drying treatment at 80° C. for 1 hour under vacuum. After the Schlenk tube was cooled to room temperature, the Schlenk tube was replaced in an inside with an argon gas and charged with 5 ml of toluene containing 100 µL of mesitylene as a standard substance, 1.2 mmol of norbornene and 2.4 mmol of dimethylchlorosilane, and then they were reacted at room temperature for 20 minutes while stirring. The catalytic activity was evaluated by a conversion rate (FIG. 9) of norbornene and a yield (FIG. 10) of the product shown in Equation 2.

Example 15

The catalytic activity was evaluated by carrying out the same procedure as in Example 14, except that the metal complex (2) obtained in Example 2 was used. The results thereof are shown together in FIGS. 9 and 10.

Comparative Example 5

The catalytic activity was evaluated by carrying out the same procedure as in Example 14, except that a solution obtained by dissolving chloroplatinic acid ($H_2PtCl_6$) in an isopropanol solvent was used. The results thereof are shown together in FIGS. 9 and 10.

Comparative Example 6

The catalytic activity was evaluated by carrying out the same procedure as in Example 14, except that the commercially available 1 weight % platinum silica catalyst (manufactured by Sigma-Aldrich Corporation) was used and that the reaction was carried out at room temperature for 60 minutes while stirring. The results thereof are shown together in FIGS. 9 and 10.

Evaluation of Catalyst Recycling

Example 16

Figure 11:
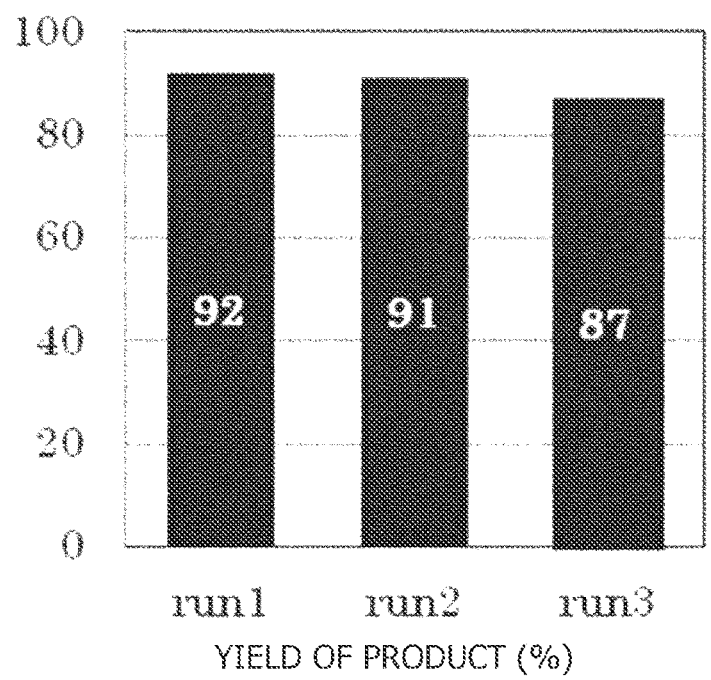
FIG. 11 is a drawing showing a change in a catalytic activity (yield of the hydrosilylation product) in the repeating several times a hydrosilylation reaction of norbornene using the supported metal complex (1) of the present invention as a catalyst.

A recycle catalytic characteristic of the supported metal catalyst (1) was evaluated by repeating several times the same procedure as in Example 14 using the supported metal catalyst (1). The results thereof are shown in FIG. 11.

INDUSTRIAL APPLICABILITY

The present invention is applicable to various technical fields using supported metal catalysts, supported metal complex catalysts and metal complex catalysts.

The invention claimed is:
1. A supported metal complex having a structure represented by the following Formula (2), in which the metal complex is fixed on an inorganic oxide:

[CHEM 2]

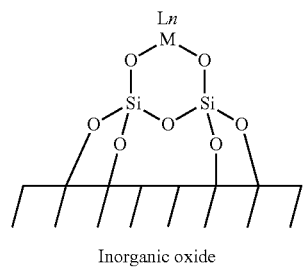

Inorganic oxide (2)

wherein M represents palladium or platinum; L represents a ligand selected from carbon monoxide, an olefin compound, an amine compound, a phosphine compound, an N-heterocyclic carbene compound, a nitrile compound and an isocyanide compound; and n represents an integer of 1 to 2 showing the number of the ligand.

2. The supported metal complex according to claim 1, wherein the inorganic oxide is silica.

3. The supported metal complex according to claim 1, wherein the inorganic oxide is mesoporous silica MCM-41.

4. A method for producing the supported metal complex as defined in claim 1, comprising contacting an organic solvent solution of a metal complex represented by the following Formula (3) with an inorganic oxide, to support the metal complex on the inorganic oxide:

[CHEM 3]

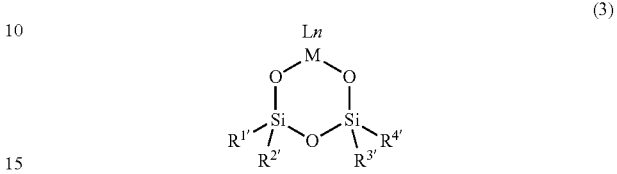

(3)

wherein M represents palladium or platinum; L represents a ligand selected from carbon monoxide, an olefin compound, an amine compound, a phosphine compound, an N-heterocyclic carbene compound, a nitrile compound and an isocyanide compound; n represents an integer of 1 to 2 showing the number of the ligand; and each of $R^{1'}$ to $R^{4'}$ represents an alkoxy group having 1 to 4 carbon atoms.

5. A catalyst for hydrosilylation reaction of olefins, comprising the supported metal complex as defined in claim 1.

* * * * *